(12) United States Patent
Bogan, Jr. et al.

(10) Patent No.: US 7,553,986 B2
(45) Date of Patent: Jun. 30, 2009

(54) PROCESS FOR THE SELECTIVE (AMM)OXIDATION OF LOWER MOLECULAR WEIGHT ALKANES AND ALKENES

(75) Inventors: Leonard Edward Bogan, Jr., Hatfield, PA (US); Fernando A. P. Cavalcanti, Lafayette Hill, PA (US); Nitin Chadda, Radnor, PA (US); Sanjay Chaturvedi, Lansdale, PA (US); Anne Mae Gaffney, West Chester, PA (US); Scott Han, Lawrenceville, NJ (US); Peter D. Klugherz, Huntingdon Valley, PA (US); Daniel Martenak, Perkasie, PA (US); Mark Anthony Silvano, New Hope, PA (US); Elsie Mae Vickery, Jenkintown, PA (US); Donald L. Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 753 days.

(21) Appl. No.: 10/993,729

(22) Filed: Nov. 19, 2004

(65) Prior Publication Data

US 2005/0137415 A1    Jun. 23, 2005

Related U.S. Application Data

(60) Provisional application No. 60/532,192, filed on Dec. 23, 2003.

(51) Int. Cl.
*C07C 253/24* (2006.01)
(52) U.S. Cl. ..................................... 558/319
(58) Field of Classification Search ................. 558/319
See application file for complete search history.

(56) References Cited

U.S. PATENT DOCUMENTS

| | | | |
|---|---|---|---|
| 4,031,135 A | 6/1977 | Engelbach et al. | |
| 4,899,003 A | 2/1990 | Manyik et al. | |
| 6,114,278 A | 9/2000 | Karim et al. | |
| 6,166,263 A | 12/2000 | Etzkorn et al. | |
| 6,383,978 B1 | 5/2002 | Bogan, Jr. | |
| 6,403,525 B1 | 6/2002 | Chaturvedi et al. | |
| 6,407,031 B1 | 6/2002 | Chaturvedi et al. | |
| 6,407,280 B1 | 6/2002 | Chaturvedi et al. | |
| 6,423,875 B1 | 7/2002 | Machhammer et al. | |
| 6,461,996 B2 | 10/2002 | Chaturvedi et al. | |
| 6,472,552 B1 | 10/2002 | Bogan, Jr. | |
| 6,504,053 B1 | 1/2003 | Chaturvedi et al. | |
| 6,589,907 B2 | 7/2003 | Chaturvedi et al. | |
| 6,624,111 B2 | 9/2003 | Chaturvedi et al. | |
| 6,645,906 B2 * | 11/2003 | Bogan et al. ................. | 502/311 |
| 2002/0123647 A1 | 9/2002 | Bogan, Jr. et al. | |

FOREIGN PATENT DOCUMENTS

| | | |
|---|---|---|
| EP | 1081124 | 3/2001 |
| EP | 1201636 A | 5/2002 |
| GB | 939713 A | 10/1963 |
| JP | 2000-327650 | 11/2000 |
| WO | WO97/36849 A | 10/1997 |
| WO | WO01/98247 | 12/2001 |
| WO | WO02/00587 | 1/2002 |

OTHER PUBLICATIONS

Database Beilstein 'Online! XP002325081.
Database Beilstein 'Online! XP002325082.
Database Beilstein 'Online! XP002325083.

* cited by examiner

*Primary Examiner*—James O. Wilson
*Assistant Examiner*—Ebenezer Sackey
(74) *Attorney, Agent, or Firm*—Marcella M. Bodner

(57) ABSTRACT

An improved process for the production of unsaturated carboxylic acids and unsaturated nitriles from their corresponding $C_3$ to $C_5$ alkanes, or mixtures of $C_3$ to $C_5$ alkanes and alkenes, that involves a multi-stage reaction system which employs both separation of the oxidation product from one or more intermediate effluent streams, as well as feeding additional oxygen to reaction zones subsequent to the first reaction zone.

15 Claims, 2 Drawing Sheets

PROCESS FOR THE SELECTIVE (AMM)OXIDATION OF LOWER MOLECULAR WEIGHT ALKANES AND ALKENES

CROSS REFERENCE TO RELATED PATENT APPLICATIONS

This is a non-provisional patent application of U.S. provisional patent application Ser. No. 60/532,192 filed Dec. 23, 2003.

FIELD OF THE INVENTION

The present invention relates to improved processes for the selective oxidation of $C_3$ to $C_5$ alkanes and alkenes, including propane and isobutane, and mixtures thereof, to their corresponding unsaturated carboxylic acids and unsaturated nitriles, including acrylic acid, methacrylic acid, acrylonitrile and methacrylonitrile.

BACKGROUND OF THE INVENTION

Unsaturated carboxylic acids, such as acrylic acid and methacrylic acid, are industrially important as starting materials for various synthetic resins, coating materials and plasticizers. Two step vapor phase reaction processes from alkenes have historically been practiced for the production of unsaturated carboxylic acids, including acrylic acid and methacrylic acid and these processes are still widely used today. These two step reaction processes typically include a first reaction step wherein an alkene, such as propylene, is converted to an intermediate hydrocarbon product, such as acrolein, and a second reaction step wherein the intermediate hydrocarbon product, such as acrolein, is converted to an unsaturated carboxylic acid, such as acrylic acid. However, in view of the price difference between propane and propene, attention has been drawn to the development of a method for producing acrylic acid and methacrylic acid by using a lower alkane, such as propane, as the starting material, and catalytically reacting the lower alkane in a gaseous phase, in the presence of a suitable mixed metal oxide catalyst. Thus, recently, processes involving single-step vapor phase catalytic oxidation of alkanes, alkenes, and mixtures thereof, to produce unsaturated carboxylic acids have been researched. More particularly, such methods involve subjecting an alkane, an alkene, or a mixture thereof, to a vapor phase catalytic oxidation reaction in the presence of a suitable mixed metal oxide catalyst, to produce the corresponding unsaturated carboxylic acid.

Unsaturated nitriles, such as acrylonitrile and methacrylonitrile, have been industrially produced as important intermediates for the preparation of fibers, synthetic resins, synthetic rubbers, and the like. The most popular method for producing such nitriles is to subject an olefin, such as propene, to a catalytic reaction with ammonia, in the presence of a suitable catalyst in a gaseous phase at a high temperature. However, in view of the price difference between propane and propene or between isobutane and isobutene, attention has been drawn to the development of a method for producing acrylonitrile or methacrylonitrile by using a lower alkane, such as propane or isobutane, as the starting material, and catalytically reacting the lower alkane with ammonia in a gaseous phase, in the presence of a suitable mixed metal oxide catalyst.

Although in most cases, the exact catalyst formulations of the most suitable catalysts for use in the commercial processes mentioned above are proprietary to the catalyst supplier, the technology is well established and such catalysts are commercially available from various sources.

While a portion of the efforts to develop efficient and economical single-step vapor phase catalytic oxidation processes for the production of unsaturated carboxylic acids and unsaturated nitrites from their corresponding alkanes and alkenes has focused on identifying and preparing suitable catalysts, the possibility also exists for improvements to the overall reaction processes which would further increase yield and conversion rates by overcoming various process limitations.

More particularly, one such process limitation concerns the potential for gaseous streams containing hydrocarbons, such as alkanes and alkenes, and oxygen to autoignite, or spontaneously explode, when the concentrations of hydrocarbons and oxygen in the same gaseous stream are too high. In order to avoid such mishaps, the amounts of alkanes, alkenes and oxygen in gaseous feed streams of such oxidation processes are typically maintained below certain levels, which depend upon the particular constituents of the feed streams and the temperatures at which they exist in the processes. This generally means that in order to maximize the amount of hydrocarbons in a given stream, the stochiometric amount of oxygen required to convert all of the hydrocarbon in the stream cannot be added to the feed stream at the beginning of the process due to flammability concerns and, therefore, a significant amount of unreacted hydrocarbon is likely to be present in the product stream. One result of these circumstances is that the processes are inefficient, i.e., wasteful of hydrocarbon feed and achieving less than optimal product yields.

To avoid the aforesaid problem of creating flammable gaseous feed streams in vapor phase oxidation reactions, it is known to employ a multi-stage reaction system, i.e., having at least two oxidation reactors, or stages, in series with one another, and an oxygen feed arrangement which is explained and referred to hereinafter as "staged oxygen arrangement". Such "staged oxygen arrangements" are discussed in connection with vapor phase oxidation reactions in, for example, U.S. Pat. No. 6,166,263, U.S. Pat. No. 4,899,003, and International Patent Application No. WO 01/98247. In addition, EP 1 081 124 A2 discloses a modified type of staged oxygen feed wherein the oxygen-containing feed stream is divided into a plurality of oxygen-containing streams that are successively introduced into a single reaction zone to facilitate the continuous conversion by catalyzed oxidation of the hydrocarbon feed.

In a reaction system having two oxidation reactors arranged in series with one another, the feed stream to the first oxidation reactor contains hydrocarbons and a less than stoichiometric amount of oxygen (such that the mixture is non-flammable), and the resulting effluent stream contains unreacted hydrocarbons, as well as by-products, along with the desired oxidation product(s). The effluent stream of the first oxidation reactor is fed to the second oxidation reactor, along with additional fresh oxygen, either pure oxygen or as part of an oxygen-containing stream (such as air) (such that the mixture is non-flammable), whereby at least some of the unreacted hydrocarbons in the stream are oxidized in the second oxidation reactor. As a result, the effluent of the second oxidation reactor contains more oxidation product and less unreacted hydrocarbon than the effluent stream of the first oxidation reactor. In addition, the staged oxygen arrangement also allows the concentration of hydrocarbons in the initial feed stream to the first oxidation reactor to be higher than that for a process arrangement without staged oxygen.

A problem has been encountered, however, relating to certain multi-stage vapor phase reaction systems that utilize a staged oxygen arrangement to enable higher hydrocarbon feed concentrations. More particularly, while the concentration of oxidation product in the effluent streams increases with each successive stage in such a multi-stage process, the overall process oxidation product yield is actually less than the yield for a comparable single stage reaction system. This problem must be addressed in order for such processes to recapture the benefits of the staged oxygen arrangement.

It is known in the art to use condensers to remove or separate certain condensable constituents from gaseous process streams, including intermediate and final stage effluent streams. For example, U.S. Pat. No. 6,166,263 discloses the use of a condenser in a single stage reaction to separate a vapor phase reaction effluent stream into a liquid product stream and a recycle gas stream which is recycled back to the reactor. WO 01/98247 discloses the use of a condenser in a two-stage vapor phase oxidation process to separate the effluent stream of the second reactor (i.e., the final stage effluent stream) into an off-gas stream, which is recycled back to the first reactor, and an aqueous carboxylic acid product stream.

U.S. Pat. No. 4,899,003 discloses the use of a condenser in a two-stage vapor phase oxidation process to treat an intermediate process stream. More particularly, the condenser removes a particular by-product (i.e., water) from the effluent of the first reactor before the effluent is fed, with additional oxygen, to the second reactor. The fact that a small amount of acrylic acid, another by-product, is also removed from the intermediate stream by the condenser is inconsequential to the goal of the disclosed process. The stated purpose of removing the water in U.S. Pat. No. 4,899,003 is to minimize the water present in the second reactor, whereby the vapor phase oxidation reaction in the second reactor is driven toward the desired product, ethylene, and away from production of by-product acetic acid.

WO 02/00587 discloses a vapor phase reaction process for converting a feed stream containing propylene and propane to hydroformylation products, such as butyraldehyde. This process involves partial condensation to separate the hydroformylation reaction effluent stream into a stream containing primarily the hydroformylation product and another gaseous stream containing primarily unreacted propylene and propane. The gaseous stream containing unreacted propylene and propane is fed to another vapor phase reaction process for producing different products, i.e., acrolein and acrylic acid. Thus, WO 02/00587 teaches subjecting the effluent stream of a first reaction process to partial condensation to recover the desired product and also to create another separate stream for feeding to an entirely separate, subsequent reaction process which produces different products.

The present invention provides a process which addresses the problem of a decreased total yield of oxidation product in multi-stage vapor phase oxidation reactions which employ staged oxygen arrangements for conversion of lower alkanes and alkenes, and mixtures thereof, to unsaturated carboxylic acids and/or unsaturated nitrites. More particularly, it has been discovered that in such processes, the removal of at least a portion of the oxidation product from each intermediate effluent stream, for example, by inter-stage partial condensation, prior to adding more oxygen and feeding the effluent stream to the next stage, unexpectedly results in overall cumulative oxidation product yields greater than either the original single-stage system or the system including only staged oxygen arrangements.

SUMMARY OF THE INVENTION

The present invention provides an improved process for the production of unsaturated carboxylic acids and unsaturated nitrites from their corresponding $C_3$ to $C_5$ alkanes, or mixtures of $C_3$ to $C_5$ alkanes and alkenes, that utilizes a multi-stage reaction system and includes the steps of separating the oxidation product from one or more intermediate effluent streams, as well as feeding additional oxygen to reaction zones subsequent to the first reaction zone.

More particularly, the process of the present invention is for producing unsaturated carboxylic acids or unsaturated nitrites by vapor phase oxidation reaction of their corresponding $C_3$ to $C_5$ alkanes, $C_3$ to $C_5$ alkenes, and mixtures thereof. The process of the present invention uses a reaction system, having at least two reaction zones arranged in series with one another and at least one catalyst capable of catalyzing the vapor phase oxidation reaction disposed in each of the at least two reaction zones. Furthermore, at least one intermediate effluent stream exits a preceding one of the at least two reaction zones and is at least partially fed to a subsequent one of the at least two reaction zones. The process of the present invention comprises separating the at least one intermediate effluent stream into at least an intermediate product stream comprising an oxidation product selected from the group consisting of an unsaturated carboxylic acid and an unsaturated nitrile, and an intermediate feed stream comprising starting materials selected from the group consisting of an unreacted $C_3$ to $C_5$ alkane, an unreacted $C_3$ to $C_5$ alkene, and mixtures thereof; feeding the intermediate feed stream to the subsequent reaction zone; and feeding an oxygen-containing gas to the subsequent reaction zone. In one alternative embodiment, two or more of the reaction zones may be contained within a single reactor vessel.

The separating step may be performed by cooling the at least one intermediate effluent stream such that at least a portion of the oxidation products condenses out of the at least one intermediate effluent stream. Such cooling may be achieved with a condenser. The separating step may, alternatively, be performed using an absorber.

In a particular application of the present invention, the $C_3$ to $C_5$ alkane, $C_3$ to $C_5$ alkene, or mixture thereof may comprise propane, propene, or a mixture thereof, and the oxidation product may comprise acrylic acid.

The process of the present invention may also comprise feeding ammonia-containing gas to each of the at least two reaction zones. In a particular application of the process, in which ammonia-containing gas is fed to each of the at least two reaction zones, the $C_3$ to $C_5$ alkane, $C_3$ to $C_5$ alkene, or mixture thereof, may comprise propane, propene, or a mixture thereof, and the oxidation product may comprise acrylonitrile.

BRIEF DESCRIPTION OF THE DRAWINGS

A more complete understanding of the present invention will be gained from the embodiments discussed hereinafter and with reference to the accompanying drawings, in which like reference numbers indicate like features, and wherein.

DETAILED DESCRIPTION OF THE INVENTION

The process of the present invention is suitable for performing selective vapor phase catalytic oxidation of $C_3$ to $C_5$ alkanes and alkenes, and mixtures thereof, to their corresponding unsaturated carboxylic acids and unsaturated nitriles, including acrylic acid, methacrylic acid, acrylonitrile and methacrylonitrile. In this regard, the term vapor phase catalytic oxidation is intended to encompass simple oxidation, as well as ammoxidation and oxidative dehydrogenation.

To facilitate discussion, the efficacy of chemical reaction processes, including the process of the present invention, may be characterized in terms of the "feed conversion" and the "product yield". More particularly, feed conversion, or simply "conversion", is the percentage of the total moles of feed (e.g., $C_3$ to $C_5$ alkanes and alkenes, such as propane and propene, or a mixture thereof) that have been consumed by the reaction, regardless of what particular products were produced. The product yield, or simply "yield", is the percentage of the theoretical total moles of the desired product (e.g., unsaturated carboxylic acids or unsaturated nitrile, such as acrylic acid or acrylonitrile, respectively) that would have been formed if all of the feed had been converted to that product (as opposed to unwanted side products, e.g. acetic acid and $CO_x$ compounds). The aforesaid terms are generally defined as follows:

$$\text{feed conversion (\%)} = \frac{\text{moles of feed converted}}{\text{moles of feed supplied}} \times 100$$

$$\text{product yield (\%)} = \frac{\text{moles of product produced}}{\text{moles of feed supplied}} \times 100$$

As used herein, the term "$C_3$ to $C_5$ alkane" means a straight chain or branched chain alkane having from 3 to 5 carbons atoms per alkane molecule, for example, propane, butane and pentane. The term "$C_3$ to $C_5$ alkene" means a straight chain or branched chain alkene having from 3 to 5 carbons atoms per alkene molecule, for example, propene, butene and pentene. As used herein, the term "$C_3$ to $C_5$ alkanes and alkenes" includes both of the aforesaid alkanes and alkenes. Similarly, when used herein in conjunction with the terms "$C_3$ to $C_5$ alkane", or "$C_3$ to $C_5$ alkene", or "$C_3$ to $C_5$ alkanes and alkenes", the terminology "a mixture thereof", means a mixture that includes a straight chain or branched chain alkane having from 3 to 5 carbons atoms per alkane molecule and a straight chain or branched chain alkene having from 3 to 5 carbons atoms per alkene molecule, such as, without limitation, a mixture of propane and propene, or a mixture of n-butane and n-butene.

Figure 1:
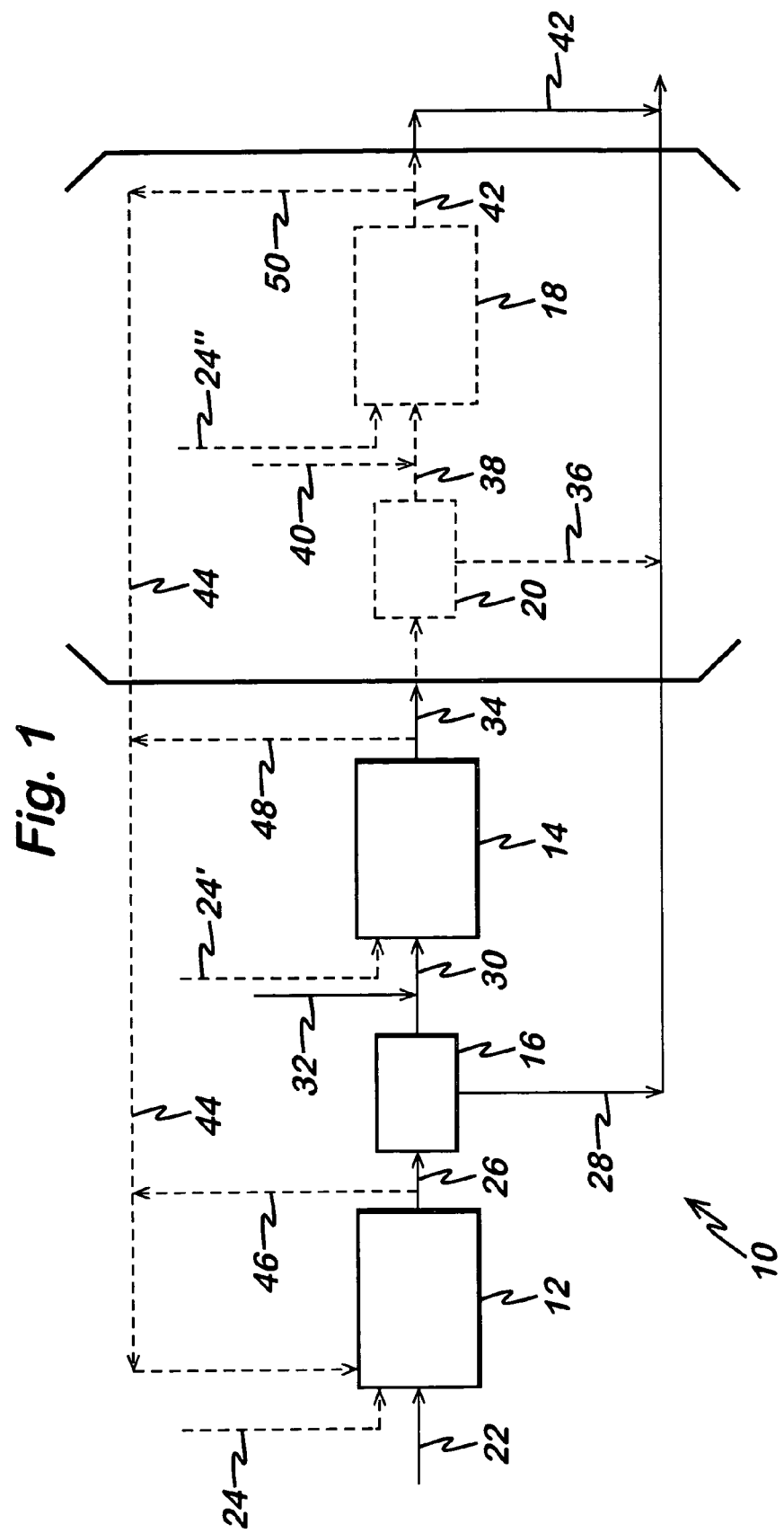
FIG. 1 is a schematic flow diagram of one embodiment of the process of the present invention.

With reference now to FIG. 1, a schematic representation is shown of a multi-stage catalytic vapor phase oxidation process 10, in accordance with the present invention, that is capable of converting a $C_3$ to $C_5$ alkane, a $C_3$ to $C_5$ alkene, or a mixture thereof (such as, for example, propane, or a mixture of propane and propene), to an unsaturated carboxylic acid (such as acrylic acid) or an unsaturated nitrile (such as acrylonitrile) in a single reaction step. The process 10 includes at least a first reaction zone (or "stage") 12 and a second reaction zone (or "stage") 14, which are arranged in series with one another such that the second reaction zone 14 is positioned downstream of the first reaction zone 12. The process 10 of the present invention also includes a separator, such as a condenser 16, which is positioned to intermediate the first and second reaction zones 12, 14, for a purpose to be described in detail hereinafter.

As shown in phantom in FIG. 1, the process 10 of the present invention may also include additional reaction zones, such as a third reaction zone (or "stage") 18 arranged in series with and downstream of the second reaction zone 14. Where the process 10 includes such additional reaction zones, it may also include additional separators, such as a second condenser 20 positioned intermediate the second and third reaction zones 14, 18, respectively, for a purpose to be described in detail hereinafter.

As used herein, an arrangement of reaction zones "in series" with one another means that the reaction zones are arranged such that at least a portion of the output stream of the first reaction zone forms at least a portion of the input stream of the second reaction zone and each successive reaction zone is similarly interconnected with the preceding reaction zone. It is noted that the portion of output stream which forms a portion of the input stream of each the successive reaction zone need not be the same with respect to amount, proportion, composition, temperature, etc., since these stream characteristics should be determined according to the requirements of the particular overall reaction system and each reaction zone, as would be readily determinable by those having ordinary skill in the art. In particular, it is noted that the reaction zones 12, 14, 18 of the present invention are arranged in series with one another, with the separators 16, 20 positioned intermediate to successive reaction zones, 12, 14 and 14, 18, respectively, for purposes which will become clear hereinafter.

Furthermore, the overall yield of oxidation product from such multiple reaction zone (i.e., "multi-stage") reaction systems is cumulative relative to each reaction zone. In other words, for example, where such a reaction system has three reaction zones and the first reaction zone provides an oxidation product yield of about 35%, the second reaction zone provides about 20% yield, and the third reaction zone provides about 10%, then the theoretical overall yield of oxidation product by the system could be expected to be about 65%. This staged oxygen arrangement has practical limitations since, as the hydrocarbons to be oxidized are consumed in successive stages, the additional oxidation product produced thereby will cease to be in amount significant enough to justify the additional reaction zones of the reactor system.

Any type of reactors that are suitable for performing the desired vapor phase oxidation reactions may be used to contain, or hold, the reaction zones 12, 14, 18 in accordance with the process 10 of the present invention. Shell-and-tube reactors, for example and without limitation, are suitable for use in connection with the process 10 of the present invention.

In addition, at least one catalyst bed (not shown, per se) is contained within each reaction zone 12, 14, 18 and comprises at least one catalyst (not shown) capable facilitating the desired vapor phase oxidation reaction. The catalyst beds may be of different types, including but not limited to fixed-bed, moving-bed and fluidized-bed. In addition, any suitable catalyst may be used and would be selected based upon the particular $C_3$ to $C_5$ alkane, $C_3$ to $C_5$ alkene, or mixture thereof, and the desired oxidation products. As is well known in the art, the catalysts may be used alone, or they may also be used together with a carrier, or support, such as, without limitation, silica, alumina, titania, aluminosilicate or diatomaceous earth. Further, depending upon the scale or system of the reaction, they may be molded into a proper shape and/or particle size. The particular shape or geometry of the catalysts are not particularly limited in connection with the present invention. The selection of the catalysts, their shape, size and packing method, are well within the ability of persons having ordinary skill in the art. For example, suitable catalysts for a variety of vapor phase oxidation reactions are described fully in U.S. Pat. Nos. 6,383,978, 6,403,525, 6,407,031, 6,407,280, 6,461,996, 6,472,552, 6,504,053, 6,589,907 and 6,624,111, each of which is hereby incorporated herein by reference.

Separators suitable for use with the present invention include any suitable fluid separator capable of separating a gaseous product stream into multiple streams according to composition, such as separating a gaseous output stream into a first stream containing primarily the desired reaction product(s) and a second stream containing primarily unreacted materials and by-products. For example, while not intending to be limited, the separator may be a partial condenser 16, 20, such as a conventional heat exchanger, capable of cooling the gaseous output stream sufficiently to condense and separate out at least a portion of the lowest boiling point components of the gaseous output stream would be suitable for use with the process 10 of the present invention. The coolant in such a condenser may be, for example, without limitation, cooling tower water having a temperature between 85° F. and 105° F. (29° C. to 40° C.), or chilled water having a temperature between 32° F. and 40° F. (0° C. and 5° C.). In addition, for example, the separators may include gas absorbers or gas adsorbers.

Suitable starting materials, which are discussed hereinafter and which are readily determinable by persons having ordinary skill in the art, are fed into the first reaction zone 12. In the first reaction zone 12, the starting materials come into contact with the catalyst and react with one another to form the desired oxidation products, as well as various side products and by-products, according to the particular types of $C_3$ to $C_5$ alkanes and alkenes used.

Suitable starting materials for the process 10 of the present invention depend upon the desired oxidation product and typically include, but are not limited to, a $C_3$ to $C_5$ alkane, a $C_3$ to $C_5$ alkene, or a mixture thereof, and an oxygen-containing gas, as well as, optionally, steam, diluting gases and ammonia. The starting materials may be added separately and simultaneously to the first reaction zone 12, or they may be mixed and fed to the first reaction zone 12 as one or more combined streams. For example, as explained in further detail hereinafter, the initial feed stream 22, shown in FIG. 1, may be a combined stream comprising an oxygen-containing gas and a $C_3$ to $C_5$ alkane, a $C_3$ to $C_5$ alkene, or a mixture thereof. The optional supplemental streams 24, 24', 24", shown in phantom in FIG. 1, may be, for example, steam-containing gases or ammonia-containing gases, depending upon the particular oxidation products desired. The optional supplemental streams 24, 24', 24" may even comprise additional $C_3$ to $C_5$ alkane, $C_3$ to $C_5$ alkene, or a mixture thereof.

The detailed mechanism of the oxidation reaction of the present invention is not clearly understood, but the oxidation reaction is carried out by oxygen atoms present in the above mixed metal oxide or by molecular oxygen present in the feed gas. Addition of oxygen-containing gas to the starting materials provides such molecular oxygen to the reaction system. The term "oxygen-containing gas," as used herein, refers to any gas comprising from 0.01% up to 100% oxygen, including, for example, air. Thus, although the oxygen-containing gas may be pure oxygen gas, it is usually more economical to use an oxygen-containing gas such as air, since purity is not particularly required.

The purity of the starting material, i.e., the $C_3$ to $C_5$ alkane, the $C_3$ to $C_5$ alkene, or the mixture thereof, is not particularly limited. Thus, commercial grades of such alkanes, or mixtures of such alkanes and alkenes, may be used as starting material for the process 10 of the present invention, although higher purities are advantageous from the standpoint of minimizing competing side reactions. In addition, mixed $C_3$ to $C_5$ alkane/alkene feeds are generally more easily obtained and may include price incentives (e.g., lower separation costs) relative to pure $C_3$ to $C_5$ alkane feeds. For example, a mixture of alkane and alkene containing a lower alkene such as ethene, a lower alkane such as methane or ethane, air or carbon dioxide, as impurities, may be used without any particular problem. Further, the starting material mixture of $C_3$ to $C_5$ alkane and alkene may be a mixture of various $C_3$ to $C_5$ alkanes and alkenes. Further details concerning the starting materials will be discussed hereinafter in connection with particular embodiments of the present invention.

Suitable diluting gases include, but are not limited to, one or more of: carbon monoxide, carbon dioxide, or mixtures thereof, an inert gas, such as nitrogen, argon, helium, or mixtures thereof. A suitable molar ratio of the starting materials for the initial feed stream 22, ($C_3$ to $C_5$ alkane, $C_3$ to $C_5$ alkene, or a mixture thereof):(oxygen):(diluting gas):($H_2O$), would be, for example, (1):(0.1 to 10):(0 to 20):(0.2 to 70), for example, including but not limited to, (1):(1 to 5.0):(0 to 10):(5 to 40).

Where it is desired to produce unsaturated carboxylic acids, it is beneficial to include steam among the starting materials. In such a case, for example, a gaseous input stream comprising a mixture of and oxygen-containing gas and a steam-containing $C_3$ to $C_5$ alkane, or a steam-containing $C_3$ to $C_5$ alkene, or a steam-containing mixture thereof, may be used. It is noted that the steam may be added to the first reaction zone 12 separately from the $C_3$ to $C_5$ alkane, the $C_3$ to $C_5$ alkene, or the mixture thereof, and the oxygen-containing gas, as an initial feed stream 22 and an optional steam stream 24, respectively (see FIG. 1). Alternatively, a steam-containing $C_3$ to $C_5$ alkane, or a steam-containing $C_3$ to $C_5$ alkene, or a steam-containing mixture thereof, and the oxygen-containing gas may be separately supplied to the first reaction zone 12. The steam to be employed may be present in the form of steam gas in the reaction system, and the manner of its introduction is not particularly limited.

When steam is supplied together with the mixture of $C_3$ to $C_5$ alkanes and alkenes, as starting material gas, the selectivity for an unsaturated carboxylic acid is distinctly improved, and the unsaturated carboxylic acid can be obtained in good yield. However, the conventional technique utilizes a diluting gas, as described above, for the purpose of diluting the starting material. Such a diluting gas is used to adjust the space velocity, the oxygen partial pressure and the steam partial pressure, as will be readily understood by persons having ordinary skill in the art.

Where it is desired to produce unsaturated nitriles, the starting materials must include ammonia. In such cases, it is possible to use an initial feed stream 22 which is a gas mixture comprising a $C_3$ to $C_5$ alkane, a $C_3$ to $C_5$ alkane, or a mixture thereof, ammonia (not shown), and an oxygen-containing gas. Alternatively, an oxygen-containing gas and a gaseous mixture comprising a $C_3$ to $C_5$ alkane, or a $C_3$ to $C_5$ alkene or a mixture thereof, and ammonia may be supplied as separate feed streams (not shown) to the first reaction zone 12.

In the process 10 of the present invention, as the starting material mixture of $C_3$ to $C_5$ alkanes and alkenes, it is suitable to use a mixture of $C_3$ to $C_5$ alkane and $C_3$ to $C_5$ alkene, for example, propane and propene, isobutane and isobutene, or n-butane and n-butene. According to the present invention, from such a mixture of an alkene and an alkane, an unsaturated carboxylic acid such as an α,β-unsaturated carboxylic acid can be obtained in good yield. For example, when propane and propene, or isobutane and isobutene, are used as the starting material mixture of alkane and alkene, acrylic acid or methacrylic acid will be obtained, respectively, in good yield. In the mixture of alkane and alkene, the alkane is present in an amount of at least 0.5% by weight up to 95% by weight, preferably at least 0.5% by weight to 10% by weight; most preferably, 0.5% by weight to 5% by weight.

As an alternative, an alkanol, such as isobutanol, which will dehydrate under the reaction conditions to form its corresponding alkene, i.e. isobutene, may also be used as a feed material to the present process or in conjunction with the previously mentioned feed streams. Suitable alkanols include, but are not limited to, normal and branched alcohols, alkyl halides, amines and other functionalized alkanes, including, but not limited to, ethanol, n- or iso-propanol, and n- or branched butanols.

It is also possible to operate the process 10 of the present invention using only a $C_3$ to $C_5$ alkane, a $C_3$ to $C_5$ alkene, or a mixture thereof, substantially in the absence of molecular oxygen. In such a case, it is preferred to adopt a method wherein a part of the catalyst is appropriately withdrawn from the reaction zone from time to time, then sent to an oxidation regenerator, regenerated and then returned to the reaction zone(s) for reuse. As the regeneration method of the catalyst, a method may, for example, be employed which comprises contacting an oxidative gas such as oxygen, air or nitrogen monoxide with the catalyst in the regenerator usually at a temperature of from 300° to 600° C.

With reference again to FIG. 1, a first effluent stream 26 exits the first reaction zone 12 and typically contains, but is not limited to, one or more oxidation products (e.g., unsaturated carboxylic acids and unsaturated nitriles), unreacted oxygen, and unreacted $C_3$ to $C_5$ alkane or alkene, or mixture thereof and, possibly, unreacted water and unreacted ammonia, depending upon the starting materials used. The first effluent stream 26 also typically contains reaction by-products, including for example, but not limited to, acetic acid and carbon dioxide.

In accordance with the present invention, at least a portion of the one or more oxidation products is separated from the first effluent stream 26, for example, by using a separator, such as the condenser 16 shown in FIG. 1, to produce an intermediate product stream 28 and an intermediate feed stream 30 (see FIG. 1). The intermediate product stream 28 typically contains, but is not limited to, at least a portion of the one or more oxidation products from the first effluent stream 26, as well as other condensables, such as organic acids, aldehydes, ketones, and water. The intermediate product stream 28 may be fed to additional processing apparatus (not shown) to undergo further separation and purification processes. The intermediate feed stream 30 contains, but is not limited to, at least a portion of the unreacted oxygen, unreacted $C_3$ to $C_5$ alkane or alkene, or mixture thereof, and possibly reaction by-products such as acetic acid and carbon dioxide, and, possibly, unreacted water and unreacted ammonia, depending upon the starting materials used.

As shown in FIG. 1, the intermediate feed stream 30 is fed into the second reaction zone 14, along with additional oxygen-containing gas 32. More particularly, the additional oxygen-containing gas 32 may be first combined with the intermediate feed stream 30 and then fed together, as a combined stream (see FIG. 1) to the second reaction zone 14. Alternatively, the additional oxygen-containing gas 32 may be fed to the second reaction zone 14 as a separate feed stream (not shown). In the second reaction zone 14, the unreacted $C_3$ to $C_5$ alkane or alkene, or mixture thereof, and the oxygen (including the unreacted oxygen already present in the intermediate feed stream 30, as well as the additional oxygen contributed by the oxygen-containing gas 32) come into contact with the at least one catalyst in the second reaction zone 14 and react with one another to form the desired oxidation products, as well as various side products and by-products, according to the particular types of alkanes and alkenes used.

A second effluent stream 34 (see FIG. 1) exits the second reaction zone 14 and typically contains, but is not limited to, one or more oxidation products (e.g., unsaturated carboxylic acid and unsaturated nitrile), unreacted oxygen, and unreacted $C_3$ to $C_5$ alkane or alkene, or mixture thereof, as well as reaction by-products which may include, but are not limited to, acetic acid and carbon dioxide and, possibly, unreacted water and unreacted ammonia, depending upon the starting materials used. The second effluent stream 34 may be fed to additional processing apparatus (not shown) to undergo separation and purification processes as is well-known to persons having ordinary skill in the art, to recover the one or more oxidation products.

The cumulative yield (%) of a particular oxidation product produced by a multi-stage oxidation reaction process, such as the process 10 of the present invention, is calculated by adding the numbers of moles of the particular oxidation product present in each of the effluent streams, dividing this sum by the number of moles of alkane (or alkane and alkene) fed to the process, and multiplying the result by 100. For example, the following formula is suitable for calculating the cumulative yield of oxidation product for the above-described process), which has a first reaction zone 12 and a second reaction zone 14:

$$\text{product yield }(\%) = \frac{\text{moles of product in first effluent stream} + \text{moles of product in second effluent stream}}{\text{moles of feed supplied}} \times 100$$

The cumulative yield of the desired oxidation product produced by the above-described process 10 in accordance with the present invention is greater than the cumulative yield of the desired oxidation product that is produced by a process that does not include both separating at least a portion of the one or more oxidation products from the first effluent stream 26, as well as feeding additional oxygen-containing gas 32 to the second reaction zone 14. In addition, the cumulative yield of the one or more oxidation products produced by the above-described process 10 in accordance with the present invention is greater than the cumulative yield of the one or more oxidation products that is produced by a process that includes only feeding additional oxygen-containing gas 32 to the second reaction zone 14, without separating at least a portion of the one or more oxidation products from the first effluent stream 26. The process 10 of the present invention allows for the use of starting materials containing a higher concentration of the $C_3$ to $C_5$ alkane, the $C_3$ to $C_5$ alkene, or mixture thereof. It is also believed that a greater portion of the oxygen in each subsequent reaction remains available for reacting and converting the $C_3$ to $C_5$ alkanes and alkenes.

With reference again to FIG. 1, and particularly the features shown in phantom, in another embodiment of the present invention, at least a portion of the one or more oxidation products are separated from the second effluent stream 34, for example, by using a second separator, such as the second condenser 20 shown in phantom in FIG. 1, to produce a second intermediate product stream 36 and a second intermediate feed stream 38 (shown in phantom in FIG. 1). The second intermediate product stream 36 typically contains, but is not limited to, at least a portion of the one or more oxidation products from the second effluent stream 34, as well as other condensables, such as organic acids, aldehydes, ketones, and water. The second intermediate product stream 36 may be fed to additional processing apparatus (not shown) to undergo further separation and purification processes. The second intermediate feed stream 38 contains, but is not limited to, at least a portion of the unreacted oxygen, unreacted $C_3$ to $C_5$ alkane or alkene, or mixture thereof, and possibly reaction by-products such as acetic acid and carbon dioxide such as acetic acid and carbon dioxide, and, possibly, unreacted water and unreacted ammonia, depending upon the starting materials used.

As shown in phantom in FIG. 1, the second intermediate feed stream 38 is fed into the third reaction zone 18 (shown in phantom), along with additional oxygen-containing gas 40. More particularly, the additional oxygen-containing gas 40 may be first combined with the second intermediate feed stream 38 and then fed together, as a combined stream (see FIG. 1) to the third reaction zone 18. Alternatively, the additional oxygen-containing gas 40 may be fed to the third reaction zone 18 as a separate feed stream (not shown). In the third reaction zone 18, the unreacted $C_3$ to $C_5$ alkane or alkene, or mixture thereof, and the oxygen (including the unreacted oxygen already present in the second intermediate feed stream 38 and the additional oxygen contributed by the oxygen-containing gas 32) come into contact with the at least one catalyst in the third reaction zone 18 and react with one another to form the desired oxidation products, as well as various side products and by-products, according to the particular types of alkanes and alkenes used.

A third effluent stream 42 (see FIG. 1) exits the third reaction zone 18 and typically contains, but is not limited to, one or more oxidation products (e.g., unsaturated carboxylic acid and unsaturated nitrile), unreacted oxygen, and unreacted $C_3$ to $C_5$ alkane or alkene, or mixture thereof, as well as reaction by-products which may include, but are not limited to, acetic acid and carbon dioxide. The third effluent stream may also contain, possibly, unreacted water and unreacted ammonia, depending upon the starting materials used. The third effluent stream 42 may be fed to additional processing apparatus (not shown) to undergo separation and purification processes, to recover the one or more oxidation products.

It is noted that the process 10 of the present invention may be suitably operated as a single-pass reaction or, alternatively, with recycle to one or more of the reaction zones 12, 14, 18, without losing the benefits achieved by the present invention. More particularly, by a single-pass vapor phase catalytic oxidation reaction is meant a vapor phase catalytic oxidation reaction wherein the reactants only pass through each of the reaction zones 12, 14, 18, i.e. over and/or through the catalyst beds, one time. There is no recycle of any unreacted reactants nor is there any recycle of reacted materials, regardless of whether they are products or by-products of the reaction. On the other hand, a vapor phase catalytic oxidation reaction with recycle would involve sending a recycle stream (shown in phantom 44) comprising at least a portion (shown in phantom 46, 48, 50) of the effluent streams 26, 34, 42, respectively, of one or more of the reaction zones 12, 14, 18, respectively, back to one or more of the reaction zones 12, 14, 18.

Figure 2:
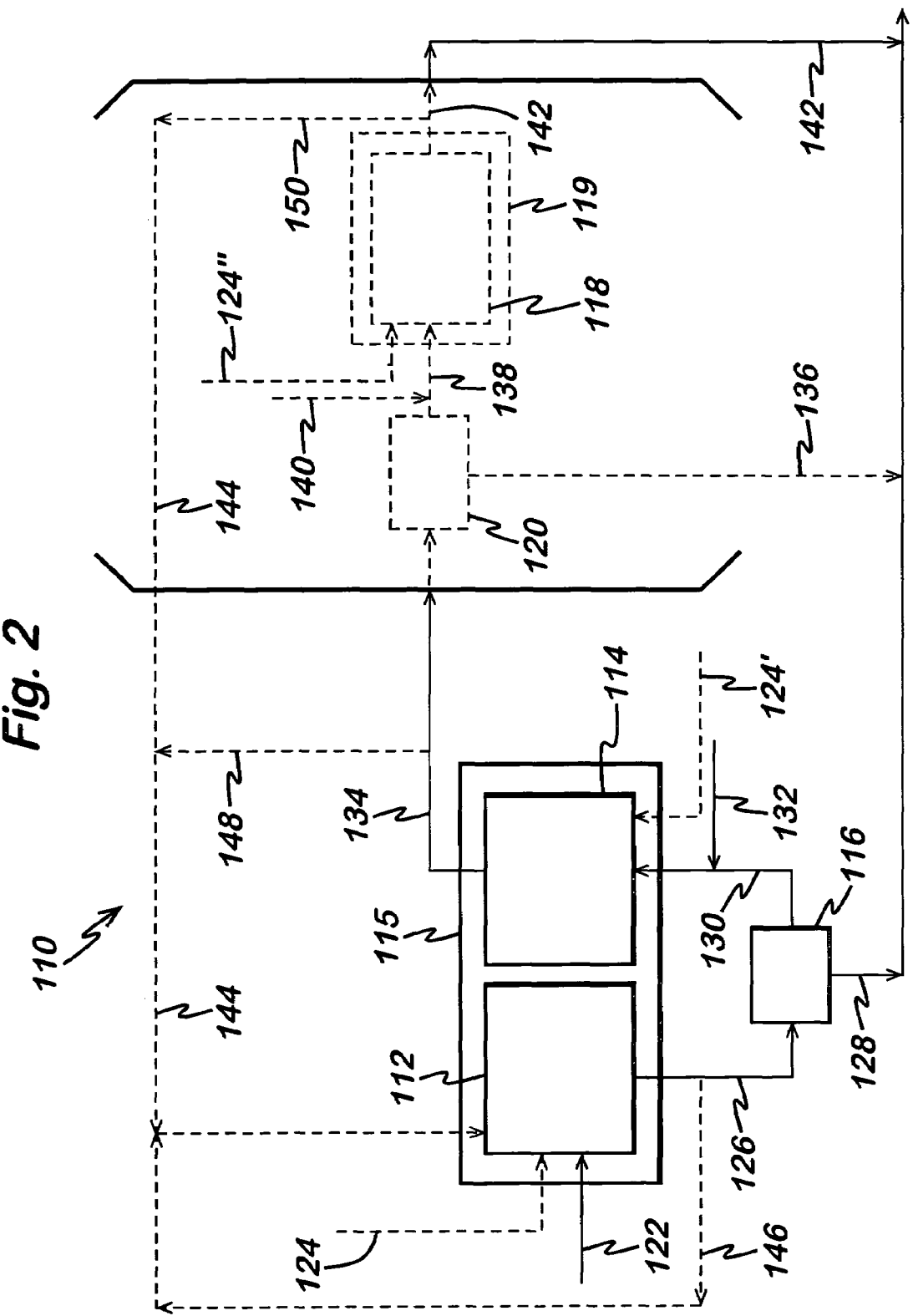
FIG. 2 is a schematic flow diagram of another embodiment of the process of the present invention.

With reference to FIG. 2, it is noted that elements illustrated in FIG. 2, which correspond to the elements described above with respect to FIG. 1, have been designated by corresponding reference numerals increased by one hundred. The alternative embodiment of FIG. 2, as well as the various elements thereof, are constructed and designated for use in substantially the same manner as the embodiment of FIG. 1 and the elements thereof, unless otherwise stated.

FIG. 2 shows an alternative embodiment of the process of the present invention that utilizes fewer reaction vessels because multiple reaction zones are contained within a single reaction vessel. More particularly, a reactor vessel 115 may be adapted to be capable of containing a plurality of reaction zones, such as first and second reaction zones 112, 114. Such a reactor vessel 115 may, for example, include an interior baffle or manifold (not shown) which divides the interior of the reaction vessel 115 into two separate heat exchange zones (not shown), i.e., one for each reaction zone 112, 114. Where the reactor vessel 115 is a shell and tube type of reactor, a first half of the tubes therein (not shown) may extend through one heat exchange zone of the reactor vessel 115 and the second half of the tubes (not shown) may extend through the other heat exchange zone. Each half of the tubes, respectively, of such a reaction vessel 115 contains a reaction zone. For example, the first half of the tubes might contain the first reaction zone 112, and the second half of the tubes would contain the second reaction zone 114. This arrangement of equipment conserves capital by requiring only one reactor vessel 115, rather than two or more, to contain two or more reaction zones. The design and construction of such reactor vessels having multiple reaction zones are well within the skill of persons having ordinary skill in the art.

With reference still to FIG. 2, in operation, the feed materials, as described hereinabove (i.e., including at least a $C_3$ to $C_5$ alkane, a $C_3$ to $C_5$ alkene, or a mixture thereof), is directed into the first half of the tubes and pass through the first reaction zone 112. As described previously hereinabove in connection with the first embodiment shown in FIG. 1, in the first reaction zone 112, the starting materials come into contact with a suitable catalyst situated therein, and react with one another to form the desired oxidation products, as well as various side products and by-products, according to the particular types of $C_3$ to $C_5$ alkanes and alkenes used. A first effluent stream 126 exits from the first half of the tubes and the reaction vessel 115 and is fed to a first separator, such as a first inter-condenser 116. The first inter-condenser 116 separates the first effluent stream 126 into a first intermediate product stream 128 and a first intermediate feed stream 130.

The first intermediate feed stream 130, which contains unreacted $C_3$ to $C_5$ alkanes or alkenes, or mixtures thereof, among other things, is then directed back into the reaction vessel 115 and the second half of the tubes, along with additional oxygen-containing gas 132. The unreacted $C_3$ to $C_5$ alkanes or alkenes, or mixtures thereof, and the additional oxygen-containing gas 132 pass through the second reaction zone 114, wherein they come into contact with a suitable catalyst situated therein, and react with one another to form the desired oxidation products, as well as various side products and by-products, according to the particular types of $C_3$ to $C_5$ alkanes and alkenes used. A second effluent stream 134 exits from the second half of the tubes and the reaction vessel 115, and passes through a second separator, such as a second inter-condenser 120. The second inter-condenser 120 separates the second effluent stream 134 into a second intermediate product stream 136 and a second intermediate feed stream 138.

The second intermediate feed stream 138, which contains unreacted $C_3$ to $C_5$ alkanes or alkenes, or mixtures thereof, among other things, may then, optionally, be fed, along with additional oxygen-containing gas 140, to a third reaction zone 118 for reaction of unreacted feed materials (i.e., unreacted $C_3$ to $C_5$ alkane or alkene, or mixture thereof, and unreacted oxygen, etc) in the manner described hereinabove in connection with FIG. 1. The third reaction zone 118 may be contained within a second, separate reactor vessel 119 by itself, as shown schematically in FIG. 2. Alternatively, the reaction vessel 119 may contain all three reaction zones 112, 114, 118 (not shown), or the third reaction zone 118 and an optional fourth reaction zone (not shown). As will be readily apparent, many variations beyond those suggested here are possible and would be well within the skill of persons of ordinary skill to design and construct.

In a manner similar to that described hereinabove in connection with FIG. 1 and the first embodiment of the present invention, optional supplemental streams 124, 124', 124", shown in phantom in FIG. 2, may be, for example, steam-containing gases or ammonia-containing gases, depending upon the particular oxidation products desired. The optional supplemental streams 124, 124', 124" may even comprise additional $C_3$ to $C_5$ alkane, $C_3$ to $C_5$ alkene, or a mixture thereof.

Notwithstanding the broad applicability of the present invention, and without intending to limit the present invention in any way, a first application of the present invention will be described in further detail with respect to a case where propene and propane are used as the starting material mixture of alkene and alkane and air is used as the oxygen source to produce acrylic acid by vapor phase oxidation, in a single step, in the presence of a suitable mixed metal oxide catalyst. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propene/propane mixture, whereby high selectivity for acrylic acid can be obtained. This reaction can be conducted usually under atmospheric pressure, but may be conducted under a slightly elevated pressure or slightly reduced pressure. With respect to other mixtures of alkene(s) and alkane(s), the composition of the feed gas may be selected in accordance with the conditions for the mixture of propene and propane. For example, the feed streams to each reaction zone 12, 14, 18 may be as follows: propane in an amount between 3 vol % and 50 vol %, such as between 7 vol % and 25 vol %, oxygen in an amount between 1 vol % and 50 vol %, such as between 5 vol % and 25 vol %, and water (steam) in an amount between 1 vol % and 50 vol %, such as 5 vol % and 25 vol %, based upon the total volume of the particular feed stream. It is noted that the compositions of the various feed streams of the process 10 need not be the same as one another in order to realize the benefits of the present invention and, in fact, may need to be different from one another, as will be readily understood and determinable by persons of ordinary skill in the art.

Typical reaction conditions for the oxidation of propane or isobutane to acrylic or methacrylic acid may be utilized in the practice of the present invention. General conditions for the process of the present invention are as follows: the reaction temperature can vary from 200° C. to 700° C., but is usually in the range of from 200° C. to 550° C., for example, 300° C. to 450° C., or even 350° C. to 400° C.; the gas space velocity, "SV", in the vapor phase reactor is usually within a range of from 100 to 10,000 $hr^{-1}$, for example, 300 to 6,000 $hr^{-1}$, or even 300 to 2,000 $hr^{-1}$; the average contact time with the catalyst can be from 0.01 to 10 seconds or more, but is usually in the range of from 0.1 to 10 seconds, for example from 2 to 6 seconds; the residence time in each reaction zone can be between 0.5 and 5 seconds, such as between 1 and 3 seconds; the pressure in the reaction zone usually ranges from 0 to 75 psig, such as, for example, no more than 50 psig.

Of course, in the process 10 of the present invention, it is important that the hydrocarbon (i.e., $C_3$ to $C_5$ alkane, or a mixture of $C_3$ to $C_5$ alkanes and an alkenes) and oxygen concentrations in the various gas streams be maintained at the appropriate levels to minimize or avoid entering a flammable regime within the reaction zones 12, 14, 18 or especially in the effluent streams 26, 34, 42 of the reaction zones 12, 14, 18. For example, it is preferred that the oxygen concentration in the effluent streams 26, 34, 42 be relatively low to minimize after-burning. In addition, operation of the reaction zones 12, 14, 18 at a low temperature (for example, below 450° C.) is extremely attractive because after-burning becomes less of a problem, which enables the attainment of higher selectivity to the desired oxidation products. The catalysts suitable for use in connection with the process 10 of the present invention, as described hereinabove, typically operate more efficiently at the lower temperature range set forth above, significantly reducing the formation of by-products (such as, but not limited to, acetic acid and carbon oxides), and increasing selectivity to the desired oxidation product (for example, but not limited to, acrylic acid). As a diluting gas, to adjust the space velocity and the oxygen partial pressure, an inert gas such as nitrogen, argon or helium may be employed.

When the process 10 of the present invention is employed to perform oxidation reaction of propane and propene, in accordance with the present invention, carbon monoxide, carbon dioxide, acetic acid, etc. may be produced as by-products, in addition to acrylic acid. The effluent streams 26, 34, 42 and, therefore, the intermediate feed streams 30, 38 also, are likely to contain unreacted water. In addition, an unsaturated aldehyde may sometimes be formed, depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it to a vapor phase catalytic oxidation reaction with a conventional oxidation reaction catalyst for an unsaturated aldehyde.

Without intending to limit the present invention in any way, another application of the process 10 of the present invention is to produce an unsaturated nitrile. Such a process comprises reacting a $C_3$ to $C_5$ alkane, or a mixture of $C_3$ to $C_5$ alkanes and an alkenes, containing at least 0.5% by weight of the $C_3$ to $C_5$ alkane, with ammonia in the presence of a suitable catalyst, as described hereinabove, to produce an unsaturated nitrile by vapor phase oxidation, in a single step.

In the production of such an unsaturated nitrile, as the starting material alkane, it is preferred to employ a $C_3$ to $C_5$ alkane such as ethane, propane, butane, isobutane, or pentane. However, in view of the industrial application of nitrites to be produced, it is preferred to employ a lower alkane having 3 or 4 carbon atoms, particularly propane and isobutane.

Similarly, as the starting material mixture of alkane and alkene, it is preferred to employ a mixture of a $C_3$ to $C_5$ alkane and a $C_3$ to $C_5$ alkene, such as propane and propene, butane and butene, isobutane and isobutene, or pentane and pentene. However, in view of the industrial application of nitriles to be produced, it is more preferred to employ a mixture of a lower alkane having 3 or 4 carbon atoms and a lower alkene having 3 or 4 carbon atoms, particularly propane and propene, or isobutane and isobutene. For example, without limitation, in the mixture of alkane and alkene, the alkane may be present in an amount of at least 0.1% by weight up to 95% by weight, including at least 0.5% by weight to 10% by weight, or even 0.5% by weight to 5% by weight, based on the total weight of the starting material mixture.

The purity of the starting material alkane is not particularly limited, and an alkane containing a lower alkane, such as methane, ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkane, such as methane, ethane, a lower alkene such as ethene, air or carbon dioxide, as impurities, may be used without any particular problem. Further, the starting material mixture of alkane and alkene may be a mixture of various alkanes and alkenes.

There is no limitation on the source of the alkane. It may be purchased, per se, or in admixture with an alkene and/or other impurities. Alternatively, it can be obtained as a by-product of alkane oxidation. Similarly, there is no limitation on the source of the alkene. It may be purchased, per se, or in admixture with an alkane and/or other impurities. Moreover, the alkane, regardless of source, and the alkene, regardless of source, may be blended as desired.

The detailed mechanism of the oxidation reaction of this embodiment of the present invention is not clearly understood. When it is desired to incorporate molecular oxygen in the starting materials, the oxygen-containing gas may be pure oxygen gas. However, since high purity is not required, it is usually economical to use air as the oxygen-containing gas.

It is possible to utilize an initial feed stream 22 which is a gas mixture comprising an alkane, or a mixture of an alkane and an alkene, ammonia and an oxygen-containing gas. However, a gas mixture comprising an alkane, or a mixture of an alkane and an alkene and ammonia, and an oxygen-containing gas may be supplied separately, or alternately, as one or more feed streams.

When the process 10 of the present invention is operated using an alkane, or a mixture of an alkane and an alkene, and ammonia that is substantially free from molecular oxygen, as the feed gas, one may employ a method wherein a part of the catalyst is periodically withdrawn and sent to an oxidation regenerator for regeneration, and the regenerated catalyst is returned to the reaction zone. As a method for regenerating the catalyst, for example, without limitation, an oxidizing gas such as oxygen, air or nitrogen monoxide may be permitted to flow through the catalyst in the regenerator usually at a temperature of from 300° C. to 600° C.

It is noted that where acrylonitrile is the desired oxidation product, the proportion of air to be supplied to the reaction zones 12, 14, 18 is important with respect to the selectivity for acrylonitrile. Namely, high selectivity for acrylonitrile is obtained when air is supplied within a range of at most 25 moles, particularly 1 to 15 moles, per mole of the propane. Moreover, the proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the aforesaid conditions for propane.

The process of this alternate embodiment of the present invention may be conducted at a temperature of, for example, from 200° C. to 480° C., such as from 250° C. to 450° C., or even from 275° C. to 400° C. The gas space velocity, SV, in each of the reaction zones 12, 14, 18 is usually within the range of from 100 to 10,000 hr$^{-1}$, such as from 300 to 6,000 hr$^{-1}$, or even from 300 to 2,000 hr$^1$. The residence time of the reactants in each reaction zone can be between 0.5 and 5 seconds, such as between 1 and 3 seconds. As a diluent gas, for adjusting the space velocity and the oxygen partial pressure, there may be used carbon monoxide, carbon dioxide or mixtures thereof; an inert gas such as nitrogen, argon, helium or mixtures thereof; or mixtures thereof. When ammoxidation of propene is conducted using the process 10 of the present invention, in addition to acrylonitrile, carbon monoxide, carbon dioxide, acetonitrile, hydrocyanic acid and acrolein may form as by-products. During operation of the process 10 of the present invention to produce unsaturated nitrites, the effluent streams 26, 34, 42 and, therefore, the intermediate feed streams 30, 38 also, are likely to contain unreacted ammonia.

In the following Examples, "propane conversion" is synonymous with "feed conversion" and was calculated in accordance with the formulas provided earlier hereinabove. Furthermore, "AA yield" means acrylic acid yield and is synonymous with "product yield" and was calculated in accordance with the formulas provided earlier hereinabove.

Unless otherwise specified, all percentages recited in the following Examples are by volume, based on the total volume of the feed or product gas stream.

The same mixed metal oxide catalyst was used for all of the Examples described in detail hereinafter. More particularly, a Catalyst of nominal composition $Mo_{1.0}V_{0.3}Te_{0.23}Nb_{0.17}Pd_{0.01}O_x$ was prepared in the presence of nitric acid and extracted with oxalic acid in the following manner: 200 mL of an aqueous solution containing ammonium heptamolybdate tetrahydrate (1.0M Mo), ammonium metavanadate (0.3M V) and telluric acid (0.23M Te) formed by dissolving the corresponding salts in water at 70° C., was added to a 200 mL rotavap flask. Then 200 mL of an aqueous solution of ammonium niobium oxalate (0.17M Nb), palladium nitrate hydrate (0.01M Pd), oxalic acid (0.155M) and nitric acid (0.24M) were added thereto. After removing the water via a rotary evaporator with a warm water bath at 50° C. and 28 mm Hg, the solid materials were further dried in a vacuum oven at 25° C. overnight and then calcined.

Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. 30 g of the solid materials were ground and added to 100 mL solution of 30% oxalic acid in water. The resulting suspension was stirred at 125° C. for 5 hrs in a Parr reactor, then the solids were collected by gravity filtration and dried in a vacuum oven overnight at 25° C. The Catalyst, thus obtained, was pressed and sieved to 14-20 mesh granules for use in the reaction system of the present invention, as follows.

For all Examples, a two-stage reaction process (i.e., having a first reaction zone and a second reaction zone in series with the first reaction zone) was used to perform vapor phase catalytic oxidation of propane (alkane) to acrylic acid (unsaturated carboxylic acid). Each of the reaction zones was packed with 5 cc of the above-described mixed metal oxide Catalyst, which was diluted 1:1 with DENSTONE®. The reaction zones were cooled using a molten salt bath.

The reaction system further included an inter-condenser between the first and second reaction zones capable of cooling the effluent stream of the first reaction zone for the purpose of separating at least a portion of the oxidation product (acrylic acid) from the effluent stream prior to being fed to the second reaction zone. The inter-condenser was a typical shell-and-tube heat exchanger familiar to persons having ordinary skill in the art.

For all of the following Examples, reactant starting materials to the first reaction zone comprising 10 vol % propane, 9 vol % water (steam), 17 vol % oxygen, with the remainder being nitrogen, were fed to the two-stage reaction process. A residence time of 1.5 seconds was maintained for the reactants in both reaction zones (stages). The temperatures of both the first and second reaction zone were maintained between 340° C. and 380° C. and they were operated at atmospheric pressure. No recycle was employed for any of the Examples. In each Example, the compositions of the effluent streams of the first and second reaction zones were analyzed using a gas chromatograph (for gas phase effluent) and a liquid chromatograph (for liquid phase effluent).

COMPARATIVE EXAMPLE 1

No separation of the oxidation product from the effluent stream of the first reaction zone was performed. Rather, the entire effluent stream from the first reaction zone was fed into the second reaction zone with additional oxygen, in the form of molecular oxygen. A second effluent stream exited the second reaction zone and contained, among other things, acrylic acid (AA) and unreacted propane. The compositions of the effluent streams of the first and second reaction zones were analyzed and the results of the compositional analysis and calculations for the effluent streams are presented in Table 1 below, in terms of feed conversion and AA yield attributable to each reaction zone.

TABLE 1

| Reaction Zone (Stage) | Salt Bath Temperature (° C.) | Reactor Peak Temperature (° C.) | Cumulative Propane Conversion (%) | Cumulative Acrylic Acid Yield (%) |
|---|---|---|---|---|
| First | 351 | 379 | 51.7 | 38.7 |
| Second | 352 | 364 | 80.1 | 50.6 |

EXAMPLE 2

A portion of the oxidation product (AA) was separated from the effluent stream of the first reaction zone using the inter-condenser operating with chilled water at a temperature of 4° C. More particularly, the inter-condenser removed greater than 95 vol % of the AA formed in the first stage from the first stage effluent stream to form an intermediate product stream containing primarily AA, as well as various other by-products, including, but not limited to, water and acetic acid.

The remaining portion of the effluent stream formed an intermediate feed stream which was fed into the second reaction zone with additional oxygen, in the form of molecular oxygen, in an amount such that the feed stream to the second reaction zone was non-flammable. A second effluent stream exited the second reaction zone and contained, among other things, acrylic acid (AA) and unreacted propane. The compositions of the effluent streams of the first and second reaction zones were analyzed and the results of the compositional analysis and calculations for the intermediate product stream and the effluent streams are presented in Table 2 below in terms of feed conversion and AA yield attributable to each reaction zone.

TABLE 2

| Reaction Zone (Stage) | Salt Bath Temperature (° C.) | Reactor Peak Temperature (° C.) | Cumulative Propane Conversion (%) | Cumulative Acrylic Acid Yield (%) |
|---|---|---|---|---|
| First | 351 | 379 | 51.7 | 38.7 |
| Second | 361 | 371 | 85.3 | 60.7 |

EXAMPLE 3

The reaction system used for this Example was identical to the reaction system used for the previous Examples, with the addition of a third reaction zone (stage) in series after the second reaction zone and a second inter-condenser positioned between the second and third reaction zones. The third reactor also contains 5 cc of mixed metal oxide catalyst. Similar to the first inter-condenser, the second inter-condenser was capable of cooling the effluent stream of the second reaction zone for the purpose of separating at least a portion of the oxidation product (acrylic acid) from the effluent stream of the second reaction zone prior to being fed to the third reaction zone.

A portion of the oxidation product (AA) was separated from the effluent stream of the first reaction zone using the first inter-condenser operating with chilled water at a temperature of 4° C. More particularly, the first inter-condenser removed greater than 95 vol % of the AA formed in the first stage from the first stage effluent stream to form an intermediate product stream containing primarily AA, as well as various other by-products, including, but not limited to, water and acetic acid.

The remaining portion of the effluent stream formed an intermediate feed stream which was fed into the second reaction zone with additional oxygen, in the form of molecular oxygen. A second effluent stream exited the second reaction zone and contained, among other things, acrylic acid (AA) and unreacted propane.

A portion of the oxidation product (AA) was separated from the second effluent stream using the second inter-condenser operating with chilled water at a temperature of 4° C. More particularly, the second inter-condenser removed greater than 95 vol % of the AA formed in the second stage from the second stage effluent stream to form a second intermediate product stream containing primarily AA, as well as various other by-products, including, but not limited to, water and acetic acid.

The remaining portion of the second effluent stream formed a second intermediate feed stream which was fed into the third reaction zone with additional oxygen, in the form of molecular oxygen. A third effluent stream exited the third reaction zone and contained, among other things, acrylic acid (AA) and unreacted propane.

The compositions of both intermediate product streams and the effluent streams of the first, second and third reaction zones were analyzed. The results of the compositional analysis and calculations for the effluent streams are presented in Table 3 below in terms of feed conversion and AA yield attributable to each reaction zone.

TABLE 3

| Reaction Zone (Stage) | Salt Bath Temperature (° C.) | Reactor Peak Temperature (° C.) | Cumulative Propane Conversion (%) | Cumulative Acrylic Acid Yield (%) |
|---|---|---|---|---|
| First | 351 | 379 | 51.7 | 38.7 |
| Second | 361 | 371 | 85.3 | 60.7 |
| Third | 346 | 357 | 95.9 | 69.3 |

From the foregoing Examples, it can be seen that the process of the present invention, including the steps of separating at least a portion of the oxidation product from effluent streams and adding additional oxygen to the remaining portion prior feeding it to subsequent reaction zones, results in higher feed conversion and higher product yield.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

What is claimed is:

1. A process for producing unsaturated carboxylic acids or unsaturated nitriles by vapor phase oxidation reaction of their corresponding $C_3$ to $C_5$ alkanes, $C_3$ to $C_5$ alkenes, and mixtures thereof, using a reaction system having at least two reaction zones arranged in series with one another and at least one catalyst capable of catalyzing the vapor phase oxidation reaction disposed in each of the at least two reaction zones, wherein at least one intermediate effluent stream exits a preceding one of the at least two reaction zones and is at least partially fed to a subsequent one of the at least two reaction zones, said process comprising the steps of:

separating the at least one intermediate effluent stream into at least an intermediate product stream comprising an oxidation product selected from the group consisting of an unsaturated carboxylic acid and an unsaturated nitrile, and an intermediate feed stream comprising starting materials selected from the group consisting of an unreacted $C_3$ to $C_5$ alkane, an unreacted $C_3$ to $C_5$ alkene, and mixtures thereof;

feeding the intermediate feed stream to the subsequent reaction zone; and feeding an oxygen-containing gas to the subsequent reaction zone.

2. The process according to claim 1, further comprising the step of feeding oxygen-containing gas to a first one of the at least two reaction zones.

3. The process according to claim 1, wherein the $C_3$ to $C_5$ alkane, $C_3$ to $C_5$ alkene, or mixture thereof comprises propane, propene, or a mixture thereof and the oxidation product comprises acrylic acid.

4. The process according to claim 1, further comprising the step of feeding steam to at least one of the at least two reaction zones.

5. The process according to claim 1, wherein said separating step is performed by cooling the at least one intermediate effluent stream such that at least a portion of the oxidation products condenses out of the at least one intermediate effluent stream.

6. The process according to claim 5, wherein said cooling is achieved using a condenser.

7. The process according to claim 1, wherein said separating step is performed using an absorber.

8. The process according to claim 1, wherein at least two of the at least two reaction zones are contained within a single reactor vessel.

9. The process according to claim 1, further comprising feeding alkanols capable of dehydrating to form their corresponding alkenes to at least one of the at least two reaction zones, wherein the alkanols are selected from the group consisting of normal and branched alcohols, normal and branched alkyl halides, normal and branched amines, and other functionalized alkanes.

10. The process according to claim 1, further comprising the step of providing the $C_3$ to $C_5$ alkane, $C_3$ to $C_5$ alkene, or mixture thereof, to each of the at least two reaction zones in an amount ranging from 7 vol % to 25 vol %, based on the total volume of starting materials being fed.

11. The process according to claim 1, wherein each of the at least two reaction zones is maintained at a temperature in the range of from 200° C. to 700° C.

12. The process according to claim 1, wherein the starting materials have a contact time with the at least one catalyst in each of the at least two reaction zones in the range of from 0.1 to 10 seconds.

13. The process according to claim 1, further comprising the step of feeding ammonia-containing gas to each of the at least two reaction zones.

14. The process according to claim 13, wherein the $C_3$ to $C_5$ alkane, $C_3$ to $C_5$ alkene, or mixture thereof comprises propane, propene, or a mixture thereof and the at least one oxidation product comprises acrylonitrile.

15. The process according to claim 14, wherein each of the at least two reaction zones is maintained at a temperature in the range of from 200° C. to 480° C.

* * * * *